United States Patent [19]

Liu et al.

[11] Patent Number: 5,609,798
[45] Date of Patent: Mar. 11, 1997

[54] HIGH OUTPUT PSL AEROSOL GENERATOR

[75] Inventors: Benjamin Y. H. Liu, North Oaks; James J. J. Sun, New Brighton, both of Minn.

[73] Assignee: MSP Corporation, Minneapolis, Minn.

[21] Appl. No.: 475,351

[22] Filed: Jun. 7, 1995

[51] Int. Cl.$^6$ .................................................. B01F 3/04
[52] U.S. Cl. .................... 261/78.2; 239/432; 239/424.5; 239/338
[58] Field of Search .......................... 261/78.2; 239/432, 239/424.5, 338

[56] References Cited

U.S. PATENT DOCUMENTS

| | | | |
|---|---|---|---|
| H799 | 7/1990 | Farthing et al. | 55/392 |
| 3,249,553 | 5/1966 | Steinberg | 261/78.2 |
| 3,774,846 | 11/1973 | Schurig et al. | 261/78.2 |
| 3,808,147 | 4/1974 | Dymet et al. | 252/305 |
| 4,007,238 | 2/1977 | Glenn | 261/78.2 |
| 4,116,387 | 9/1978 | Kremen, Jr. et al. | 261/78.2 |
| 4,177,945 | 12/1979 | Schwartz et al. | 261/78.2 |
| 4,243,396 | 1/1981 | Cronenberg | 239/338 |
| 4,380,505 | 4/1983 | Wittenhorst | 252/359 R |
| 4,459,219 | 7/1984 | Kiley | 252/305 |
| 4,636,364 | 1/1987 | Geyer et al. | 422/162 |
| 4,674,491 | 6/1987 | Brugger et al. | 239/338 |
| 4,855,112 | 8/1989 | Adcock | 422/186.23 |
| 4,917,830 | 4/1990 | Ortiz et al. | 261/18.1 |
| 4,963,289 | 10/1990 | Ortiz et al. | 252/305 |
| 4,992,206 | 2/1991 | Waldron | 252/305 |
| 5,008,048 | 4/1991 | Ryder | 261/78.2 |
| 5,030,253 | 7/1991 | Tokuhiro et al. | 261/78.2 |
| 5,059,351 | 10/1991 | Carlon et al. | 252/408.1 |
| 5,059,352 | 10/1991 | Carlon et al. | 252/408.1 |
| 5,160,664 | 11/1992 | Liu | 252/305 |
| 5,301,878 | 4/1994 | Sinclair et al. | 239/338 |

FOREIGN PATENT DOCUMENTS 9246 of 1887 United Kingdom .

OTHER PUBLICATIONS

*A Condensation Aerosol Generator for Producing Monodispersed Aerosols in the Size Range, 0.0.36μ to 1.3μ*, by Benjamin Y.H. Liu, "Journal de Recherches Atmospheriques", pp. 397–406, 1966.

*A Submicron Aerosol Standard and the Primary, Absolute Calibration of the Condensation Nuclei Counter*, By Benjamin Y.H. Liu and David Y.H. Pui, "Journal of Colloid and Interface Science", vol. 47, No. 1, Apr. 1974.

*Primary Examiner*—Tim R. Miles
*Attorney, Agent, or Firm*—Westman, Champlin & Kelly, P.A.

[57] ABSTRACT

An atomizer includes a housing that has a plurality of atomizing nozzles which will atomize a solution containing small particles that are to be carried in an output aerosol. The atomizer nozzles are surrounded by a ring-like surface against which the atomized material impinges to collect large droplets and to cause secondary atomization of the liquid impinging on the ring-like surface. The ring-like surface can have many different cross-sectional configurations for obtaining different results in secondary atomization and droplet collection.

12 Claims, 7 Drawing Sheets

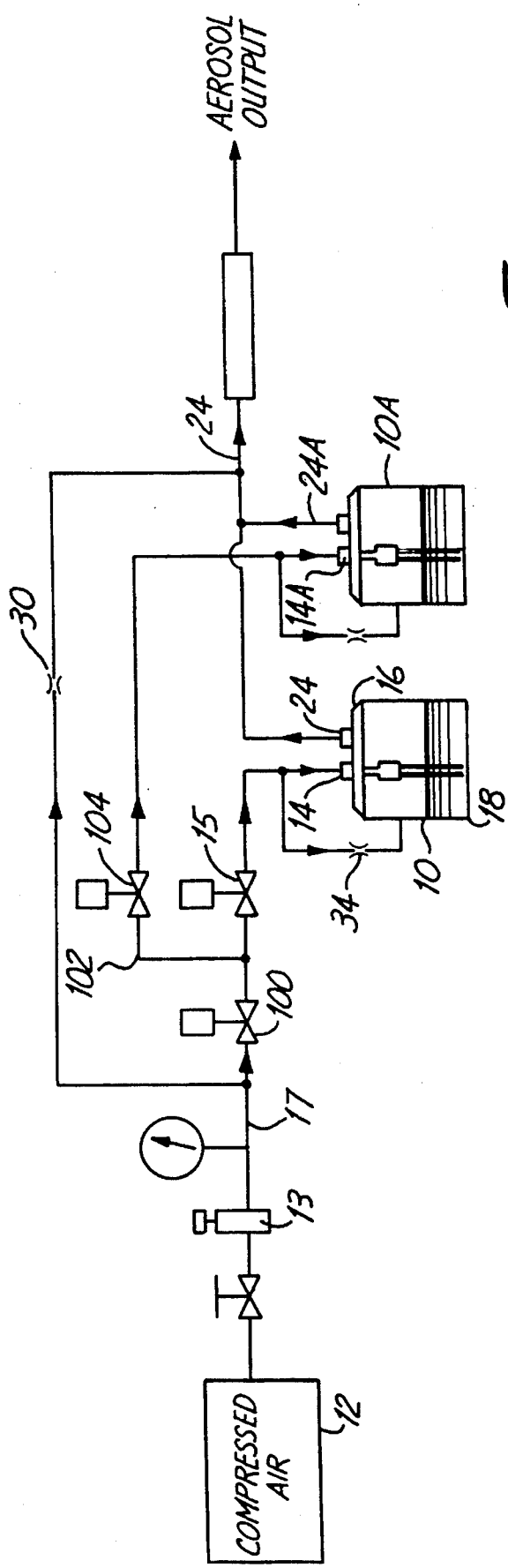

HIGH OUTPUT PSL AEROSOL GENERATOR

BACKGROUND OF THE INVENTION

The present invention relates to an aerosol generator that will deliver a high volume of polystyrene latex (PSL) spheres of a uniform particle size to form an aerosol spray, under precise control.

Fibrous and membrane filters are widely used in industrial gas cleaning systems to remove suspended particulate matter in air or other gases to avoid product contamination by the suspended particles. In critical applications, a high efficiency filter is needed. Filters of the highest efficiency are usually referred to as High Efficiency Particulate Air (HEPA) filters. The traditional HEPA filter is defined as a filter with efficiencies of 99.97% based on tests made with di-octyl phthalate (DOP) aerosols of 0.3 µm diameter. In recent years, filters of efficiencies higher than 99.97% have been developed. These filters are referred to as Ultra-Low Penetration Air (ULPA) filters. ULPA filters usually have efficiencies that are equal to or higher than 99.999%. Filters with 6-nine efficiencies (99.9999%), or 7-nine efficiencies (99.99999%) are also commercially available. These filters are widely used in the semiconductor and microelectronics industries for air filtration in cleanrooms. Other significant users of HEPA and ULPA filters include the nuclear industry, the pharmaceutical and biotechnology industries, hospital operating rooms, and other facilities in the health care industry, among others.

Before a HEPA or an ULPA filter can be accepted for use in a cleanroom, it must be tested to make sure that its efficiency is equal to or higher than that specified by the manufacturer. Although di-octyl phthalate (DOP) is widely used as the aerosol material by the nuclear and pharmaceutical industries for testing high efficiency filters, its use in the semiconductor and microelectronics industries is very limited. DOP is an oily substance with a finite vapor pressure. Following testing by DOP, the filter is contaminated by the collected oil droplets, which will evaporate over long periods to cause organic contamination of the cleanroom air. For this reason, DOP is generally not acceptable in the semiconductor and microelectronics industries.

A method that is becoming more popular for testing HEPA and ULPA filters in the semiconductor and microelectronics industries is the polystyrene latex (PLS) aerosol test. In the PSL test, an aqueous suspension of the PSL spheres of a uniform particle size is prepared, which is then atomized to form an aerosol spray. By evaporating the water from the atomized droplets, a uniform suspension of PSL spheres in air is obtained. These PSL spheres are then used as the aerosol challenge for testing the filter. The filter efficiency can be measured by counting the particles upstream and downstream of the filter by a laser particle counter, or other light scattering particle counters. The size of PSL spheres to be used for HEPA and ULPA filter testing in the semiconductor and microelectronics industry is usually specified by the buyer of the filters. PSL sphere sizes of 0.15 µm and 0.2 µm are quite common. Filter testing by DOP and other aerosol sources are specified in a number test standards.

Two methods have been used to atomize the PSL suspension so far by those involved in filter testing for the cleanroom industry. In one method, the PSL suspension is atomized by an ultrasonic nebulizer. The nebulizer output is then fed to the filter test system to form an aerosol challenge for the filter. In another method, a compressed air nebulizer of the type used for medical applications is used for atomization. In both cases, because the output of the nebulizer is quite small—typically from 0.1 cubic foot per minute (cfm), to approximately 1 cfm—and the challenge air flow for the filter is quite large (typically 800 cfm for a 2 foot×4 foot filter) it is necessary to use many nebulizers in parallel in order to produce an adequate aerosol concentration in the challenge air flow for filter testing. Sometimes as many as twenty nebulizers must be used in parallel to generate an aerosol at a high enough flow rate to produce a sufficient particle concentration for filter testing.

A second problem with the current method of generating PSL spheres for aerosol testing is that the nebulizers that are currently available produce relatively coarse droplets that result in high consumption rate for the PSL suspensions. Since uniform sized PSL suspensions are very expensive, the cost of PSL consumed for these tests is also very high. It is not uncommon for a manufacturer to spend as much as $1,000 per day for PSL spheres in testing filters.

SUMMARY OF THE INVENTION

The present invention relates to an aerosol generator system for generating polystyrene latex spheres in an atomizer that will produce fine droplets and exceptional high output rates. The atomizer includes a unique atomizer head which utilizes compressed gas forming jets issuing through a plurality of nozzles to create a low pressure region causing liquid to be drawn up from a reservoir. The liquid is atomized by the high velocity gas jet to form droplets, under a shearing action that causes the liquid to be broken up into the droplets covering a wide range of sizes. The atomized liquid is impinged against a ring-shaped solid surface that is in close proximity to the outlet of the gas jet. This ring-shaped solid surface serves as an impact ring for large droplets that are carried to the ring. The large droplets are removed from the output aerosol stream by this impingement. As the high velocity gas jet flows over the solid ring-shaped surface, it also causes the collected liquid on the surface to be re-atomized. The gas jet velocity is sufficient to cause secondary atomization to occur.

The ring-shaped surface on which the gas jet impinges acts as a large droplet collector and secondary itemization site, and greatly increases the number of fine droplets produced. Since the PSL spheres are uniformally distributed in the liquid, the number of PSL spheres thus carried in the aerosol by the atomizer also greatly increases, leading to a greatly increased output rate of the spheres per unit of air flow through the atomizer.

The atomizer jets are generally arranged in annular or peripheral configuration around a center housing, and the ring-shaped surface is on an outer housing that also conforms to the cross-sectional shape of the atomizer jet housing and has surfaces facing the jets. The cross-sectional shape of this ring-shaped impact surface can be varied for different results, and includes tapered, part spherical, cylindrical, cup shaped and planar surfaces, and other configurations as desired.

BRIEF DESCRIPTION OF THE DRAWINGS

FIG. 12 is a schematic representation of a modified atomizing system using two atomizers made according to the present invention.

DETAILED DESCRIPTION OF THE PREFERRED EMBODIMENTS

Figure 1:
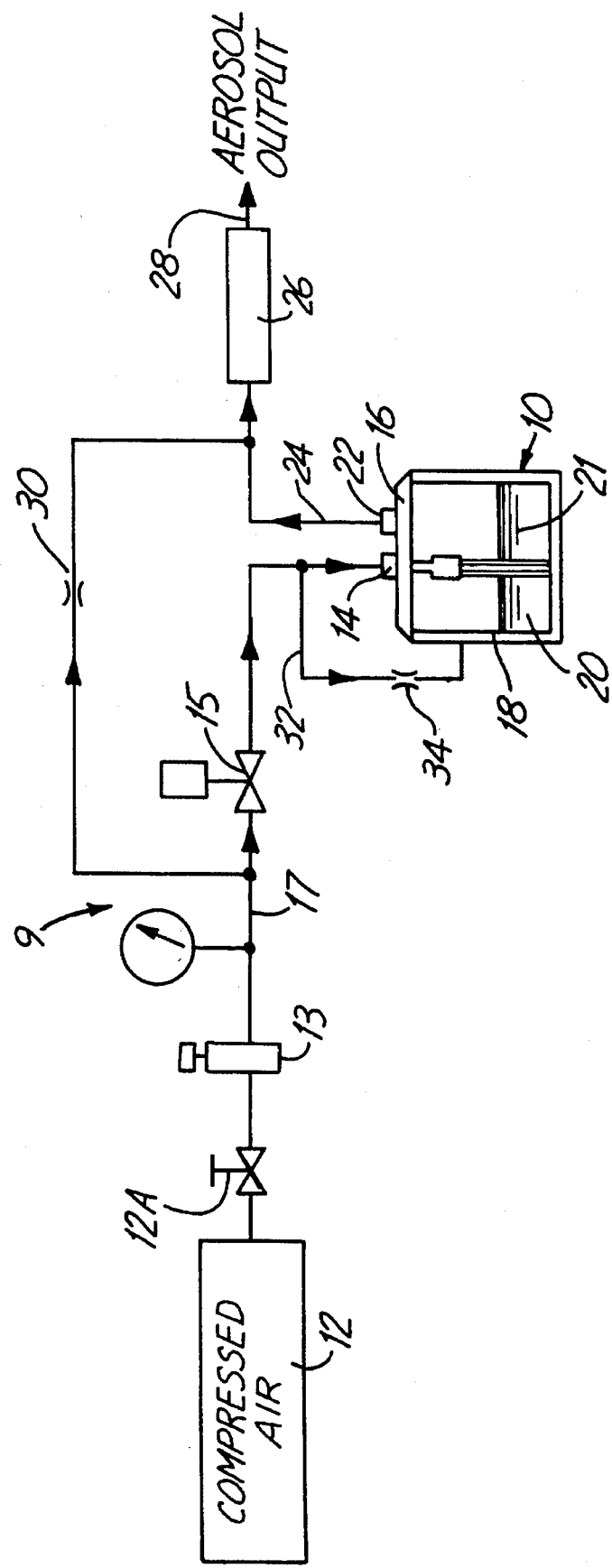
FIG. 1 is a schematic representation of an atomizing system including an atomizer made according to the present invention.

Referring first to FIG. 1, a schematic representation of atomizer system 9 is illustrated. The atomizer system includes an atomizer 10, which is connected in a fluid circuit leading from a compressed air source 12 through a suitable regulating valve 12A, and a pressure regulator 13, and through a line 17 to a solenoid valve 15. The output end of the solenoid valve 15 is connected to a fitting 14 at the top of the atomizer 10, and this fitting extends through the cover 16 (see FIG. 2). The cover 16 is on a reservoir or housing 18, that has an interior chamber 20, that holds a liquid indicated at 21 to be atomized. Liquid 21 includes a quantity of PSL spheres of know size, maintained in a suspension.

The outlet fitting 22 will carry the atomized materials from the reservoir 18 into an outlet line 24. The outlet line 24 leads to an electrostatic charge neutralizer 26 which provides an aerosol output to a desired location along a line 28. The neutralizer 26 is to remove particle static charges, so that the particles will more easily remain in the atomized material.

It can be seen that a bypass orifice indicated at 30 is connected in a line between line 17 and the output line 24, so that there will be a bypass flow of gas through this orifice 30 to provide dry gas to the outlet line 24.

Additionally, a line 32 is connected to line 17 on the exterior of the atomizer housing or reservoir 18, and is also connected through the wall of the reservoir through an orifice 34. The orifice 34 is adjusted so that it will provide interior pressure inside the reservoir 18 at a desired level during operation, but the pressure supplied to the reservoir is at a reduced level from line 17.

The pressure regulator 13 will usually be set to maintain the pressure in the line 17 between 50 psi and 100 psi. A suitable gage can be used in this line as disclosed.

Figure 2:
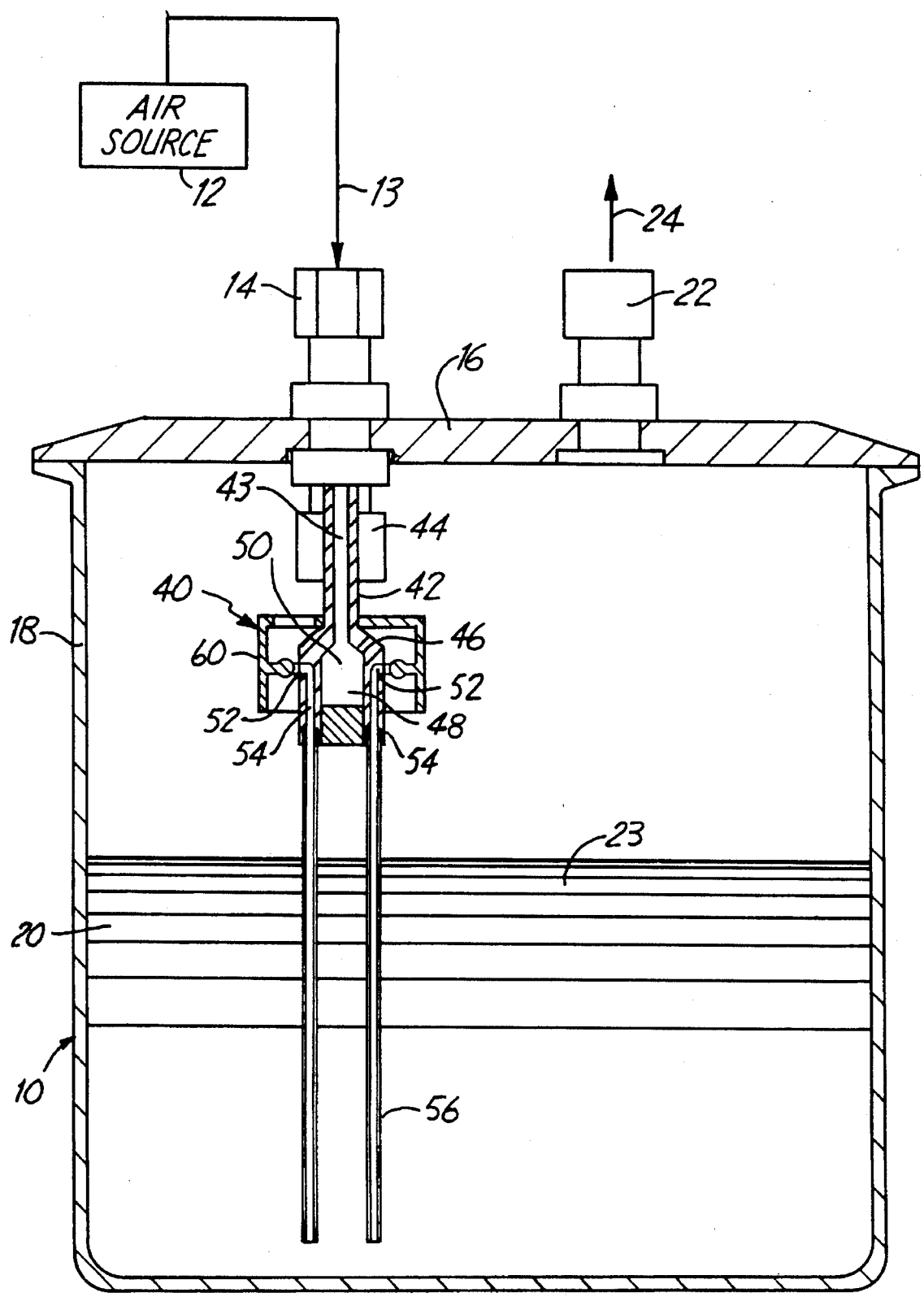
FIG. 2 is a sectional view of an atomizer made according to the present invention.
Figure 3:
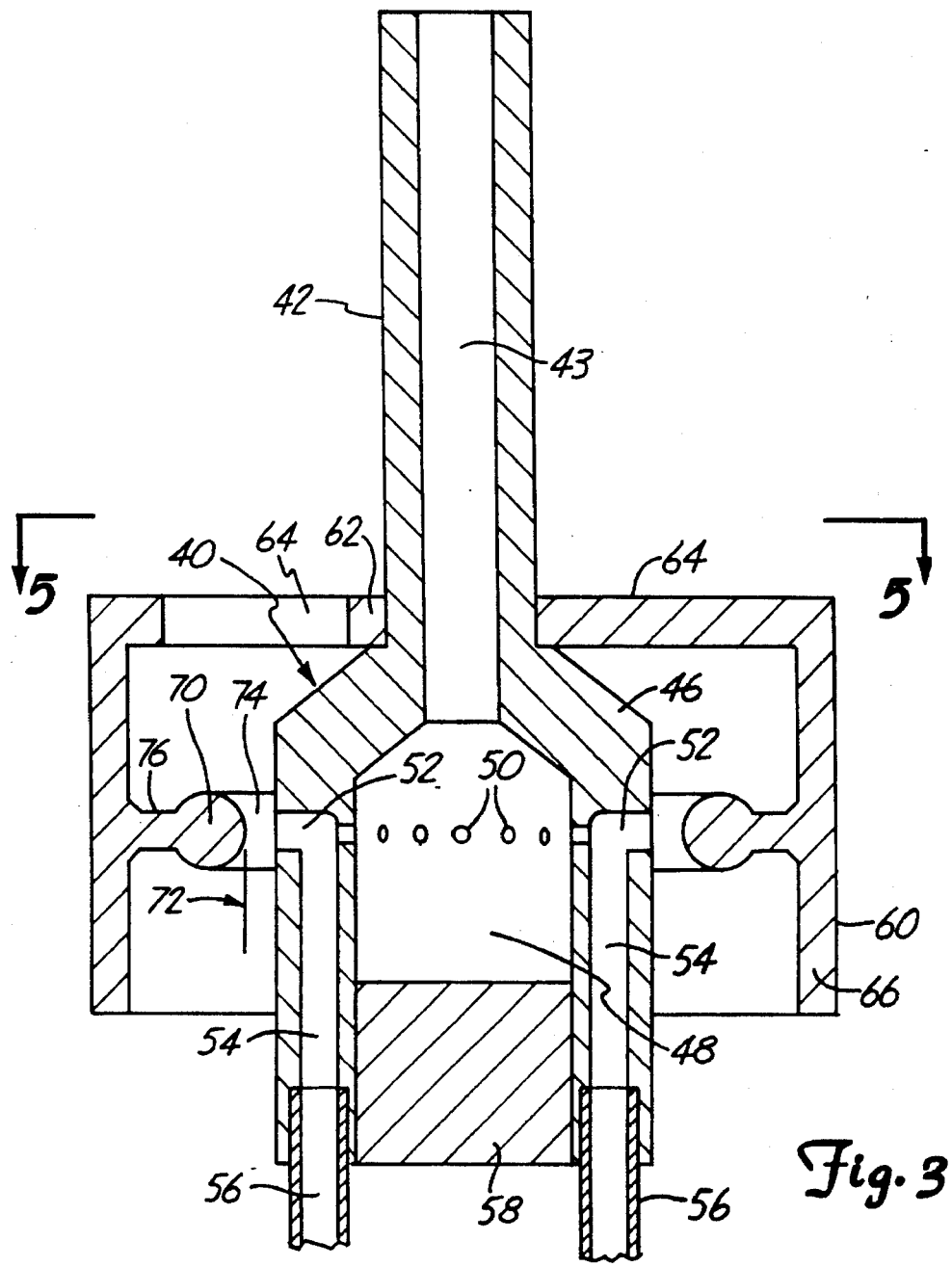
FIG. 3 is a vertical sectional view of the atomizer nozzle and an outer impaction ring carrying housing used with the atomizer of FIG. 1.
Figure 4:
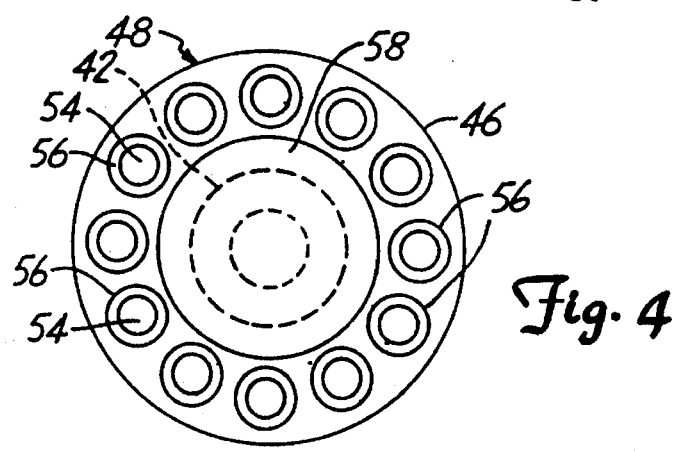
FIG. 4 is a bottom plan view of the nozzles of FIG. 3.

Referring specifically to FIGS. 2, 3 and 4, an atomizing head 40 has an input stem of 42 that is held in a bottom portion 44 of the fitting 14. The fitting 14, as shown, is retained on the cover 16, and thus supports the stem 42 when the fitting 44 is clamped tightly. The atomizer head 40 further includes a jet nozzle housing 46, that has an interior chamber 48 that receives air or gas under pressure from the line 17 through the passageway 43 of the stem 42. The wall of chamber 48 has a plurality of small jet orifices or openings 50 around the periphery thereof. These jet openings 50 open into individual nozzles 52. The nozzles 52 have outlet ports that face radially outward from the center axis of the atomizer head 40, and the high velocity jets of air coming out of aligning jet openings 50 pass through the outlet ports of the nozzles, radially out from the center of the atomizer head. The jet of air reduces the pressure in an associated aspirating passageway 54 formed in the body of the atomizing head 46 and opening to the respective nozzle 52. Each of the aspirating passageways 54 has a counterbore at its lower end, which is made to receive an aspirating tube 56 that extends down into the liquid 23 carrying the PSL particles.

As shown, and as can be seen in FIG. 4, there are several of the aspirating tubes 56 arranged around the head or housing at 46. The chamber 48 is plugged at its lower end with a suitable plug 58 so that the air under pressure in chamber 48 is forced out through the jet openings 50 as a velocity sufficient to cause a lower pressure in the aspirating passageways 54 and thus by suction draw liquid 23 up into the tubes 56, into the passageways 54, and then radially out through the nozzles 52.

The high velocity gas jets through the jet openings 50 impinges on aspirated liquid to form droplets as the liquid moves from the passageways 54 and outwardly through the nozzles. A shearing action of the high velocity gas jet causes the liquid to be broken up into droplets that are in a wide range of sizes. In the usual compressed air atomizer, both the large and small diameter droplets are carried by the outward air flow to the outside of the atomizer reservoir, and much of the atomized liquid is carried out in the form of large diameter droplets in the prior units. The large diameter droplets have a high volume, in comparison to the volume of small diameter droplets and this will cause a substantial volume of liquid to be carried outside the reservoir in prior units. For instance, a drop of 10 μm in diameter will carry away the same volume of liquid as 1,000 droplets of 1 μm diameter, since the volume of a spherical droplet is proportional to the droplet diameter to the third power.

Figure 5:
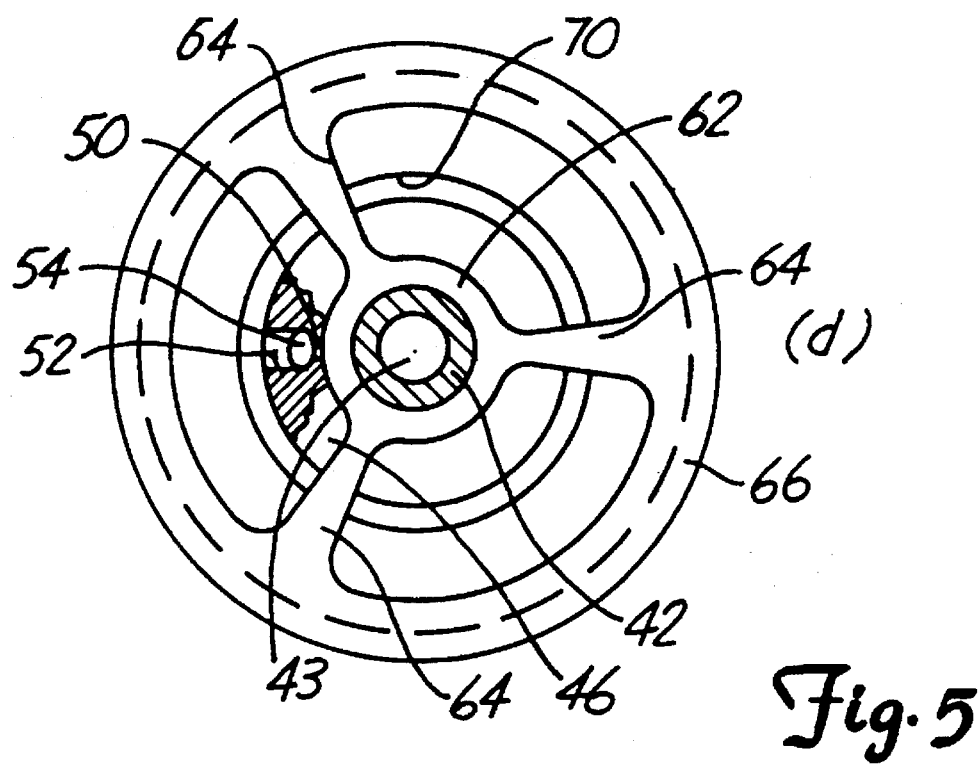
FIG. 5 is a sectional view taken on line 5—5 in FIG. 3.

The outer housing 60 is part of the atomizer assembly 40 and is a droplet size control housing. Housing 60 has a top wall that comprises a hub 62 (see FIG. 5) that is supported with arms 64 back to an annular skirt 66 that depends from the arms 60, as shown. The hub 62 rests on an upper part of the housing 46, and surrounds the stem 42. A depending skirt 66 is of a diameter so it is spaced outwardly from the head 46, and extends part way down the axial length of the head The skirt 66 carries an annular interior droplet size control ring 70 that has a desired cross-sectional shape when viewed along a radial cross-section taken parallel to the axis of each of the jet openings 50.

The ring 70 is spaced from the outlet port of each of the nozzles 52 a selected amount, generally as indicated by the double arrows 72 in FIG. 3. The liquid aspirated up through the passageways 54 is discharged out through the nozzles 52 as droplets, by action of the air jets from the jet nozzles 50, and impinges against an encompassing peripheral surface 74 that is part of the ring 70. In the form shown the ring 70 is generally part spherical in cross-section and held to the skirt 66 with a web 76. The part spherical cross section provides a curved or rounded surface against which the droplets will impinge.

The ring-shaped solid surface is placed in close proximity to the atomizer jets and serves two purposes. The large droplets that are aspirated up and discharged out through the nozzles 52 are carried by their momentum in impact onto the surface 74. The large droplets are, therefore, removed from the output aerosol stream. The high velocity gas jet flows over this ring-shaped or peripheral solid surface 74, and causes the collected liquid on the surface to be re-atomized because of the high velocity air flow over the ring-shaped surface. This high velocity air flow impinging on the ring-shaped peripheral surface 74 is sufficient to cause secondary atomization of collected liquid to occur. It has been found that the use of such a peripheral encircling ring-shaped surface as a large droplet collector and secondary atomization site, greatly increases the number of fine droplets produced. Since the PSL spheres are uniformly distributed in the liquid, the number of PSL spheres thus carried in the output aerosol by the atomizer also greatly increases, leading to an increased output rate in the PSL spheres per unit of air flow through the atomizer.

As shown in FIG. 4, the head 46 is cylindrical, and the aspirating passageways 54, and the tubes 56 are arranged so their centers are on a circle around the central axis of stem 42. This circular arrangement of the nozzle is the most convenient, with a total of 12 nozzles that can be arranged circumferentially around the central stem, with each nozzle being an equal distance from the stem axis. By arranging the nozzles at a larger diameter circle, more nozzles can be fitted in around each compressed air inlet stem. As many as 20, 30 or more nozzles can be arranged around a single stem without making the unit too large to operate.

The housing 60, as shown with the part spherical ring-shaped or peripheral surface 74 on which the atomized droplets impinge, can be modified, as shown in FIGS. 6, 7, 8 and 9.

Figure 6:
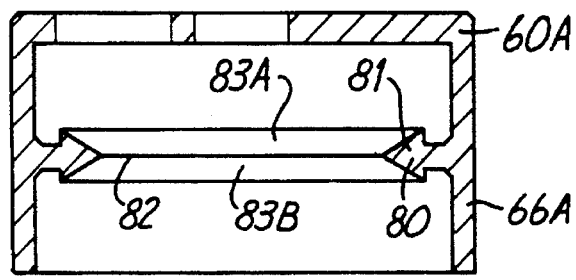
FIGS. 6, 7, 8 and 9 are cross-sectional views similar to that shown in FIG. 3 illustrating different cross sections of the impaction ring used with the present invention.

Referring specifically to FIG. 6, a housing 60A, which has the same dimensions and construction as housing 60, has a skirt 66A that supports a ring-shaped or annular ring member 80 that has a cross-sectional shape at its inner end portion 81 that is triangular shaped. The ring surface tapers to a line 82 and has tapering surfaces 83A and 83B leading away from the nozzles 52 of central housing 46 (which is not shown in FIG. 6). This will permit a different effect on atomization, as the particles are discharged from the nozzles 52 and move up the surfaces 83A and 83B.

Figure 7:
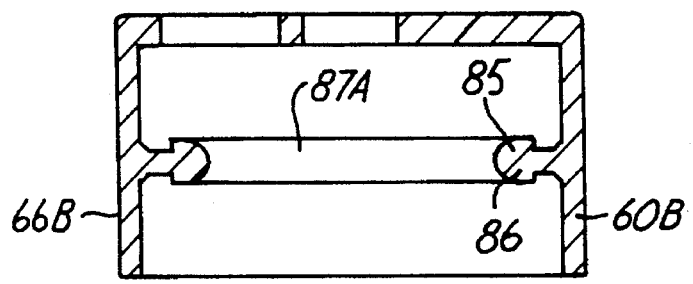

In FIG. 7, a housing 60B has a skirt 66B supporting an annular ring-shaped member 85 that has an inner end 86 that is formed generally in a shape of an end of an ellipse. The rounded inner peripheral or ring-shaped surface forms a surface 87A that is somewhat similar to a part spherical surface.

Figure 8:
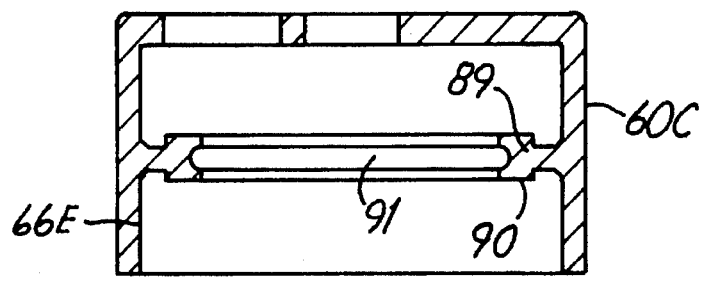

FIG. 8 shows a housing 60C that has a skirt 66C an annular ring-shaped impaction surface member 89 thereon, which has an inner end 90 that forms a ring around the central housing 46, and the end 90 has a concave groove 91 in the center portions thereof directly aligned with the axes of the nozzles 52, so that the air and aspirated particles have to impinge on the concave surface of groove 91. The groove 91 forms the concave surface of groove 91. The groove 91 forms an annular channel to catch droplets, which then must flow outwardly before the droplets can exit the reservoir through the fitting 22 and line 24.

Figure 9:
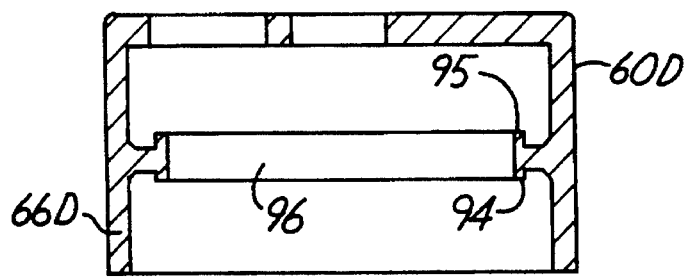

In FIG. 9, a housing 60D is shown with a skirt 66D supporting a ring member 94 that has an inner annular end portion 95 forming a flat cylindrical ring or peripheral surface that is generally perpendicular to the axis of the nozzle. This surface 96 forms a blunt surface against which the aspirated particles in the air jet impinge.

Each of these surfaces, including the elliptical end 86 shown in FIG. 7, the flat surface or blunt surface 96 in FIG. 9, and the concave surface, as well as the arrowhead surface, all provide different results, but all serve to break up the particles and promote secondary atomization.

Figure 10:
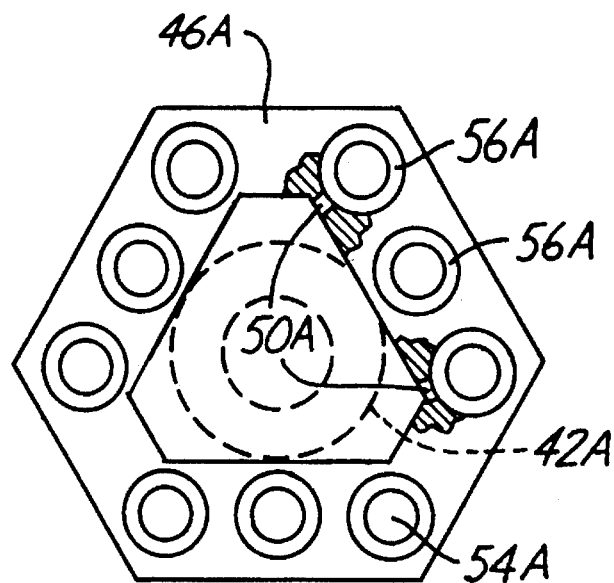
FIGS. 10 and 11 are representations of modified forms of the nozzle housing taken as bottom views similar to the view of FIG. 4.
Figure 11:
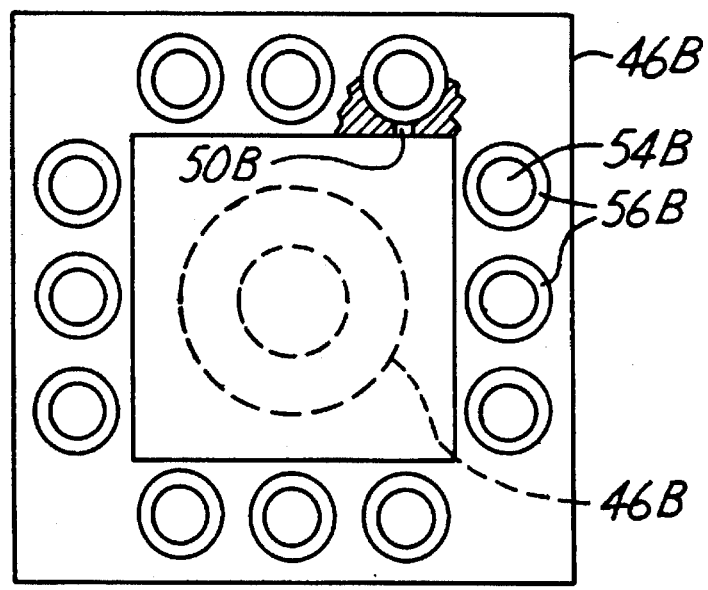

Further, the preferred circular orientation of the aspirating passages 54 and tubes 56, can be modified as exemplified in FIGS. 10 and 11 for illustrative purposes. It is to be understood that additional shapes of the housing 46 can be used.

For example, in FIG. 10, hexagon shaped housing 46A is illustrated. In this form, the ends of tubes 56A are shown, and are held in walls of the hexagon shaped housing 46A that corresponds to housing 46. The stem 42A, which is circular, is illustrated in dotted lines in FIG. 10, and it can be seen in two broken away sections that small jet passages 50A between the center chamber are provided into nozzles that are connected openings to the aspirating passages 54A and the tubes 56A in the housing. There will be different flow path lengths to the individual aspirating passages 54A, from the central axis of the housing, so that the flow characteristics may be different. However, the different cross section housing 46A may be useful in certain applications.

In FIG. 11, a rectilinear housing 46B is provided. As shown the housing is square but can be rectangular. The housing has a wall with aspirating passages 54B on the four sides of the square, supporting tubes 56B. The central stem is shown in dotted lines at 46B. Jet openings shown representatively in FIG. 11 at 50B where the housing is partly broken away, provide for a jet of high velocity air entering into a nozzle chamber in the same manner as the form of the invention shown in FIG. 3.

Referring back to FIG. 1, the atomizing system provides a dry compressed air or dry nitrogen from the source, when atomized particles are to be provided. The solenoid valve 15 can be operated to control operation of the atomizer. When there is an external demand for the aerosol containing the PSL particles, the solenoid valve 15 is turned on, and the resulting atomized droplets in line 24 are mixed with the dry compressed air flowing through the orifice 30 to form a dry PSL aerosol for filter testing. Since the PSL spheres are normally charged, the aerosol is passed through the electrostatic neutralizer 26 to reduce the electrostatic charge to a minimum.

When the demand for the aerosol ceases the solenoid valve 15 can be shut off to stop production of PSL spray by the atomizer immediately. This means that the atomizer can be turned on or off for the duration of the test, leading to further reduction in the consumption of PSL particles suspended in the liquid in the atomizer reservoir.

The atomizer as shown provides a highly efficient atomization, because of the secondary atomization carried out, and the removal of large droplets from the output at the impingement ring. The use of a solenoid valve control for permitting turning on and off the atomizer as desired also aids in reducing consumption of the liquid PSL suspension used for filter testing.

To obtain improved operational features, the atomizing system shown in FIG. 12 can be utilized. In FIG. 12, which is similar to FIG. 1 and has similar numbers. A second atomizer 10A is connected into the line 24 leading to the neutralizer 26, so that the output line 24 will carry the outputs of two atomizers that are controlled. In order to accomplish use of two atomizers, a second solenoid 100 is placed upstream of the solenoid 15, that is, between the connection of the orifice 30 in line 17 and the solenoid valve 15. Then, between the valves 100 and 15, a line 102 is connected and a third solenoid valve 104 is placed in the line 102. The output of solenoid valve 104 in turn is connected to a fitting 14A on the atomizer 10A. The atomizer 10A will operate exactly as previously explained for atomizer 10, whenever the solenoid valve 104 is turned on. The output line 24A from atomizer 10A is connected to the output line 24 which leads to the electrostatic neutralizer. The use of two atomizers as shown has several advantages, including permitting providing particles of different sizes in atomizer 10 and 10A, so that a mix of particle sizes could be obtained, or individual particle sizes can be delivered from the respective atomizer.

Using the same size particles, such as PSL spheres, in both atomizers, doubles the output of the generating system with only one atomizer. It is also clear that three, four or more atomizers can be connected into a single system to increase the versatility of the atomizer of the present invention.

Although the invention is intended primarily for producing PSL aerosols for filter testing, the aerosol generating system can also be used to produce other test aerosols for filter testing or for other purposes. If a material such as sodium chloride is needed as the aerosol material, it can be dissolved in water. The solution can then be placed in the atomizer to produce droplets of sodium chloride solution. Upon evaporation the solution droplets will give rise to a solid sodium chloride aerosol. These aerosols can be useful when used with light scattering particle counters to measure the filter efficiency as a function of particle size, since modern light scattering aerosol particle counters usually have the ability to both count the size and the number of air born particles simultaneously.

The use of the outer ring surface that is around the periphery of the high velocity air atomizing jets results in a high efficiency atomizer by breaking up large droplets and collecting them, and then causing secondary atomization of some of the droplets that are in the ring. Excess liquid will drip back into the reservoir from the peripheral ring.

This minimizes the number of large droplets that are discharged from the atomizer and as stated previously greatly increases efficiency.

Although the present invention has been described with reference to preferred embodiments, workers skilled in the art will recognize that changes may be made in form, and detail, without departing from the spirit and scope of the invention.

What is claimed is:

1. An aerosol generator system comprising a central gas conduit having a plurality of spaced nozzles positioned around the gas conduit and facing outwardly, each nozzle being connected to a source of liquid, a source of gas under pressure connected to the central conduit and providing a high velocity jet of gas through each nozzle causing a reduction in pressure for atomizing a liquid from the source of liquid through the discharge nozzle, and a ring surrounding the nozzles and having an impingement surface in proximity to but spaced outwardly from and aligned with the discharge nozzles on which the gas and atomized liquid impinges, a support for the ring spaced outwardly from the ring, the ring being unobstructed in direction above and below the ring, said impingement surface causing large droplets to collect thereon for removal from the gas, the high velocity gas flowing along and around the impingement surface, and also causing secondary atomization by the high velocity gas moving across the impingement surface, the high velocity gas being fee to move in both directions relative to a central plane of the ring.

2. The system of claim 1, wherein said impingement surface has a substantially part spherical cross-section when taken substantially parallel to the direction of movement of the jet of gas toward the surface.

3. The system of claim 1, wherein said impingement surface has a concave cross-section taken on a plane generally parallel to an axis of the jet of gas impinging on the surface.

4. The system of claim 1, wherein the surface on which the atomized material impinges has a triangular cross-section when taken on a plane generally parallel to the axis of the jet of gas impinging the surface, with a point of the triangle facing the gas jet.

5. The system of claim 1, wherein the surface on which the aerosol impinges has a part elliptical cross-section when taken on a plane parallel to the direction of flow of gas.

6. The system of claim 1, wherein the surface on which the droplets impinge has lines lying on the surface which are perpendicular to the axis of the gas impinging on the surface.

7. The system of claim 1, wherein the nozzles are mounted in a central chamber in a housing, the gas under pressure being provided to the central chamber, and a separate jet opening from the central chamber to the each one of the nozzles to provide a plurality of atomizing nozzles.

8. The system of claim 7, wherein the housing has an outer cylindrical surface through which the nozzles extend.

9. The system of claim 7, wherein a cross-section of the housing taken perpendicular to a central axis of the central chamber is generally rectilinear and the nozzles are arranged in a rectilinear configuration around the central chamber.

10. The system of claim 7 wherein a cross-section of the housing taken perpendicular to a central axis of the central chamber is a polygon, and the nozzles are arranged in a polygonal configuration around the central chamber.

11. The aerosol generator system of claim 1, wherein the support for the ring comprises a substantially peripheral wall supporting the ring and spaced outwardly from the ring.

12. The aerosol generator system of claim 11, wherein the peripheral wall extends on both sides of the plane of the ring, the peripheral wall providing openings in both directions from the plane of the ring.

* * * * *

UNITED STATES PATENT AND TRADEMARK OFFICE
CERTIFICATE OF CORRECTION

PATENT NO. : 5,609,798
DATED : March 11, 1997
INVENTOR(S) : Liu et al.

It is certified that error appears in the above-indentified patent and that said Letters Patent is hereby corrected as shown below:

Column 8, line 8, delete "fee" and insert --free--.

Signed and Sealed this

Eighth Day of July, 1997

Attest:

Attesting Officer

BRUCE LEHMAN

Commissioner of Patents and Trademarks